(12) United States Patent
Kölby-Falk

(10) Patent No.: US 6,824,535 B2
(45) Date of Patent: Nov. 30, 2004

(54) ABSORBENT ARTICLE

(75) Inventor: Ewa Kölby-Falk, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 89 days.

(21) Appl. No.: 10/005,151

(22) Filed: Dec. 7, 2001

(65) Prior Publication Data

US 2002/0072725 A1 Jun. 13, 2002

Related U.S. Application Data

(60) Provisional application No. 60/251,505, filed on Dec. 7, 2000.

(51) Int. Cl.$^7$ .............................................. A61F 13/15
(52) U.S. Cl. .................... 604/385.03; 604/387
(58) Field of Search ................. 604/385.01, 385.03, 604/386, 387, 389, 390, 385.17; 602/54, 55

(56) References Cited

U.S. PATENT DOCUMENTS

| | | | | |
|---|---|---|---|---|
| 2,742,903 A | * | 4/1956 | Lightner | 604/387 |
| 3,906,952 A | * | 9/1975 | Zamist | 604/372 |
| 4,072,151 A | * | 2/1978 | Levine | 604/387 |
| 4,536,181 A | * | 8/1985 | Cook | 604/387 |
| 5,074,855 A | * | 12/1991 | Rosenbluth et al. | 604/385.17 |
| 5,383,868 A | * | 1/1995 | Hyun | 604/385.17 |
| 5,618,281 A | | 5/1997 | Betrabet et al. | |
| 5,658,270 A | | 8/1997 | Lichstein | |
| 5,683,373 A | * | 11/1997 | Darby | 604/385.01 |
| 5,702,381 A | * | 12/1997 | Cottenden | 604/385.01 |
| 5,820,578 A | * | 10/1998 | Johansen | 602/57 |
| 6,135,988 A | * | 10/2000 | Turner et al. | 604/387 |
| 6,156,818 A | * | 12/2000 | Corzani et al. | 523/111 |
| 6,316,524 B1 | * | 11/2001 | Corzani et al. | 523/111 |
| 6,319,238 B1 | * | 11/2001 | Sartorio et al. | 604/330 |

FOREIGN PATENT DOCUMENTS

| | | |
|---|---|---|
| EP | 0 336 578 | 10/1989 |
| EP | 1 044 667 | 10/2000 |
| GB | 2 284 767 A | 6/1995 |
| WO | 95/16424 | 6/1995 |
| WO | 96/29968 | 10/1996 |
| WO | 98/28023 | 7/1998 |
| WO | 98/51249 | 11/1998 |
| WO | 98/55065 | 12/1998 |
| WO | 99/01094 | 1/1999 |
| WO | 00/30585 A1 | 6/2000 |
| WO | 00/40197 A1 | 7/2000 |

* cited by examiner

*Primary Examiner*—Weilun Lo
*Assistant Examiner*—C. Lynne Anderson
(74) *Attorney, Agent, or Firm*—Burns, Doane, Swecker & Mathis, L.L.P.

(57) ABSTRACT

The invention relates to an absorbent product, such as a sanitary towel, a panty liner or an incontinence pad, having a longitudinal direction and a transverse direction, including a liquid-permeable surface layer (102, 302), a liquid-blocking surface layer ) 103, 303) and an absorption body (104, 304) arranged between the two surface layers (102, 103; 302, 303), two side edges (105, 106; 305, 306) extending substantially in the longitudinal direction, a front edge (107, 307), a rear edge (108, 308), a front section (109, 309) and a rear section (110, 301), the width of the rear section (110, 301) not exceeding 40 mm, and a fastening member (112, 312) to be fastened to the body of a user. The product is essentially triangular in shape and the fastening member (112, 312) is applied to the liquid-permeable surface layer (102, 302) only in the rear section of the product.

11 Claims, 2 Drawing Sheets

ABSORBENT ARTICLE

This application claims priority under 35 U.S.C. §§119 and/or 365 to Provisional Application No. 60/251,505 filed in United States on Dec. 7, 2000; the entire content of which is hereby incorporated by reference.

TECHNICAL FIELD

The invention relates to an absorbent product, such as a sanitary towel, a panty liner or an incontinence pad, having a longitudinal direction and a transverse direction, comprising a liquid-permeable surface layer, a liquid-blocking surface layer and an absorption body arranged between the two surface layers, two side edges extending substantially in the longitudinal direction, a front edge, a rear edge, a front section and a rear section, the width of the rear section not exceeding 40 mm, and a fastening member to be fastened to the body of a user.

BACKGROUND ART

It is previously known to fasten absorbent products to the body by means of glue. See, for example, document WO 95/16424, WO 96/29968 and WO 98/28023.

The first two publications show products which are fastened around their periphery, i.e. within the region which is not to absorb fluid. The last-named publication (which is an example from a series of applications comprising 15 applications in total) describes a glue composition and specifies that the glue is preferably applied around the periphery of an absorbent product.

It has become increasingly common for women to wear a thong, as it is known, i.e. briefs having an extremely small rear section. The use of previously known body-fixed absorbent products together with a thong creates problems. The problem is that these products are designed for use together with conventional briefs and the product will therefore stick out beyond the edges of the thong, which may produce unsightly edge lines or creases on the clothes. Some of the discretion which is the very purpose of wearing a thong is thereby forfeited.

It has therefore been proposed to provide absorbent products intended for wear in connection with a thong. Absorbent products of this kind are designed with a very narrow rear section, which has the effect that the available liquid-receiving surface is smaller than for conventional absorbent products. Matching the known body-fixed absorbent products to the shape of a thong would result in a product having a substantially limited liquid-receiving surface, since the already limited available liquid-receiving surface would be further diminished as a result of glue being applied around the periphery of the product. This would result in a product having inadequate absorption properties and a heavily increased leakage risk as a consequence of fluid running onto the surface of the product and out over the edges thereof. In addition, there is a risk of the glued surfaces of such a product attaching to the sensitive mucous membranes of the user. Another problem with such a product, which is in close contact with the body, is that the passage of air and water vapour is hampered, which means that the product might eventually feel damp and hence uncomfortable to wear. In addition, there is a high risk of the glue sticking in the hairs of the user, which, apart from causing discomfort upon removal after use, also increases the risk of fluid leaking out over the edges of the product during use, since the product is not in close contact with the body.

There is thus a requirement to be able to provide a body-fixed absorbent product intended for wear together with a thong.

DESCRIPTION OF THE INVENTION

With the present invention, an absorbent product of the type discussed in the introduction has been realized, which product essentially avoids the above-stated problems. An absorbent product according to the invention is primarily characterized in that it is essentially triangular in shape and in that a fastening member is applied to the liquid-permeable surface layer only in the rear section of the product.

The fastening member has a fastening surface intended to be applied to the perineum of the user. As a result of the product being fastened to the perineum, the available liquid-receiving surface of the product will not significantly be affected.

A product according to the invention advantageously has a certain dimensional stability and rigidity. The rigidity of the product is important to prevent the product getting twisted, bent, cracked or torn during use. A product according to the present invention advantageously has flexural rigidity, at least in the longitudinal direction. In order to achieve the requisite rigidity in the product, together with maintained comfort, it is possible to use a plurality of materials of different rigidity. The product can thus have less rigid regions right out on the periphery of the product, the necessary flexural rigidity being obtained by virtue of a more rigid intermediate middle section.

Examples of more rigid materials suitable for use in the central part of the middle section are relatively thick layers of polypropylene film, polyethylene film and bonded fibre networks. By a relatively thick material layer is meant in this context a material layer having a layer thickness greater than ca. 0.2. mm. It is further possible to increase the rigidity of a plastics layer by mixing the plastic with talcum, chalk or some other rigidity-enhancing filler. The rigidity of the central part of the middle section can further be produced by means of rigid metal or wooden inlays, such as plates, rods, skeleton-like structures, or the like. The less rigid outer parts advantageously consist of one or more layers of soft, pliable material, such as plastics films and non-woven layers of the type commonly used as casing materials on absorbent products. The outer parts can further comprise absorbent materials, such as absorbent non-woven layers, cellulose fluff layers, tissue layers, or the like.

In order to achieve sufficient rigidity in the finished structure, it has been shown that the intrinsic rigidity of at least one component in the product should at least be greater than 100 N, measured according to ASTM D 4032-82 "Circular Bend Procedure", which method is extensively described in EP 0 336 578. By rigidity is here meant the rigidity of a planar material layer.

The fact that the product has a certain dimensional stability and rigidity enables the product to be fixed tight against the body with just one fastening member. The product is easy to apply to the body, moreover, since only one fastening point fixes the product to the body. By fastening the product to the body within a region which is free from hair, the benefit is attained of fixing the product tight against the body. This increases the capacity of the product to adapt to the body of the user, thereby reducing the risk of leakage.

As a result of the adaptability of the product to the shape of the body, the product remains securely in place, even with the extremely small fastening surface arranged on the rear section of the product. During use, the product is in close contact with the body, thereby producing a controlled and well-defined target area for the secreted body fluid. This means that the absorption body of the absorbent product can be shaped such that the absorbent material is utilized to optimum effect.

According to one embodiment of the invention, the fastening surface is constituted by low-absorbency, self-bonding adhesive. Here, a low-absorbency adhesive means an adhesive which has sufficient adhesion to skin to ensure secure fastening of the product, whilst at the same time the adhesion is not so strong that it causes harm or injury when the product is removed. The self-bonding adhesive can be constituted, for example, by polyacrylates. In order to provide extra softness, the self-bonding adhesive can be slightly foamed, producing a slight padding of the fastening surface.

The fastening surface can also be constituted by friction agents, which can be made from a material of the tack-free hot metal type, for example. A suitable hot metal material for use in this connection is a material based on thermoplastic rubber, for example styrene-isoprene rubber (SIS), styrene-butadiene rubber (SBR), or styrene-ethylenebutadiene-styrene rubber (SEBS). Other hot metal materials can also be used, for example within the following groups: ethylene vinyl acetate copolymers, cellulose acetate butyrate, ethyl cellulose and acrylic materials.

Other examples of friction agents are foam-type materials and water-based materials, for example polyvinyl acetate.

According to another embodiment, the fastening surface can be constituted by hydrogel. The hydrogel is made from a material which does not irritate the mucous membranes of the user and can comprise polymers based on vinyl alcohol, polyacrylate, polymethacrylate, polyethylene oxide, polysaccharide, acrylamide, vinyl pyrrolidone, polyethers, amino acids or urethane, and mixtures, copolymers and derivatives thereof.

It is also possible to pre-treat the hydrogel, before it is applied to the product, in such a way that it has been fully dehydrated or at least to such an extent that the hydrogel is able to reabsorb liquid when exposed to wetting during use in an absorbent product. The hydrogel will hereupon absorb body fluid and swell to its original, predetermined shape, whilst at the same time acquiring a sticky surface which produces an adhesion of the product to the perineum of the user in a kind and gentle and comfortable manner. In the course of the absorption, a suction force is also created in the hydrogel, which helps the product to be held tight against the body of the user.

It is also, of course, possible for the fastening surface to be constituted by glue similar to that which is found within wound protection, for example sticking plaster.

It is also important for the fastening surface to be constituted by material which is neither irritating to the skin, nor causes discomfort when the product is removed.

The fastening surface arranged on the product according to the present invention can have a variety of shapes, such as, for example, rectangular, circular or triangular. It is also, of course, possible for the fastening surface to be constituted by a regular or irregular pattern of dots or dashes, for example.

It has been shown in measurements that the length of the perineum does not vary significantly amongst different women. The length of the perineum has thus been shown to range between 1 and 4 cm. The length of the perineum means the distance between the vaginal opening and anal orifice of the woman.

According to one embodiment of the invention, the fastening surface has a width of max. 15 mm in the transverse direction of the product and a length of max. 20 mm in the longitudinal direction of the product. If the fastening surface is circular in shape, its radius should not exceed 7.5 mm.

According to one embodiment of the invention, the fastening member is arranged in such a way that the distance from the rear edge of the product to the periphery of the fastening surface is max. 10 mm. The product will in this case have a tongue, which will be constituted by the region between the rear edge of the product and the periphery of the fastening surface. Such a tongue facilitates fastening of the product and also the removal of the product after use.

According to a further embodiment of the invention, the rear section of the product, in the region of the fastening member, has a width of max. 20 mm.

It is advantageous if the absorbent product follows the edge of the briefs, so that the possible liquid-receiving surface is as large as possible. A product offering the maximum possible width is also important from the leakage aspect. The risk of both lateral leakage past the briefs and staining of the latter is reduced, since the product is adapted to the shape of the briefs. The absorbent product according to the invention therefore has side edges which are curved in the direction in towards a centre line extending in the longitudinal direction of the product. Curved side edges also result in the product having an anatomically adapted shape. A product which follows the shape of the thong will also be very well concealed during use.

It has been shown that the front part of the majority of thongs on the market is sufficiently wide to allow the front section of the product to be designed with more freedom according to the absorbency requirements which might pertain. In order to fit in a thong, it has proved expedient for a product according to the invention to have a width ratio in the transverse direction of the product, between the front section of the product and the rear section of the product, which is within the range of 2:1–4:1.

To prevent the product, during use, extending so far back that it is clearly visible when worn together with a thong, it is expedient for the rear section of the product to have a length ranging from 80 mm to 140 mm and for the total length of the product to be no greater than ca. 260 mm.

BRIEF DESCRIPTION OF THE FIGURES

The invention will be described in greater detail below with reference to the illustrative embodiments shown in the appended drawings, in which.

DESCRIPTION OF ILLUSTRATIVE EMBODIMENTS

Figure 1:
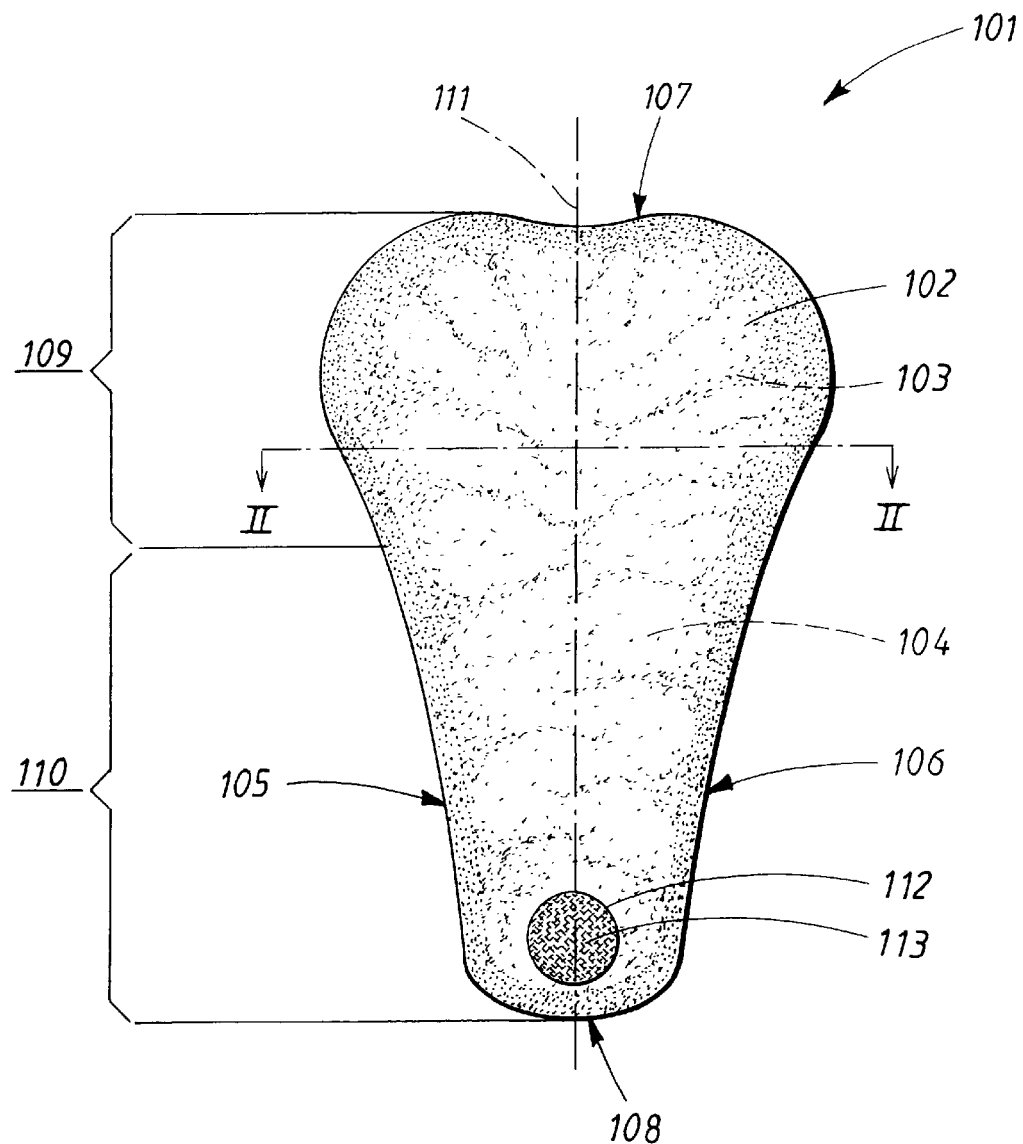
FIG. 1 shows a plane view of a panty liner viewed from the side which is intended to be facing the user when the panty liner is in use.
Figure 2:
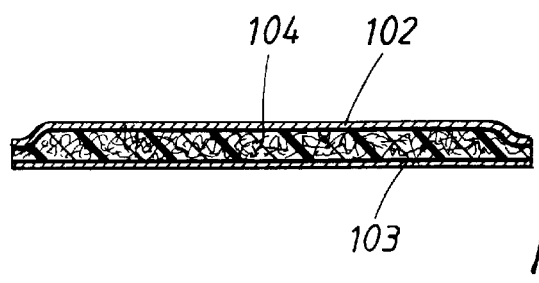
FIG. 2 shows a section along the line II—II through the panty liner in FIG. 1.

FIGS. 1 and 2 show a panty liner 101 having an essentially triangular shape with a longitudinal direction and a transverse direction. The panty liner 101 comprises a liquid-permeable surface layer 102 arranged on the side of the panty liner 101 which is intended to be facing a user during use, a liquid-blocking surface layer 103 arranged on the side of the panty liner 101 which is intended to be facing away from the user during use. Arranged between the two surface layers 102, 103 there is an absorption body 104. The panty liner 101 has two substantially longitudinal side edges 105, 106, two short sides constituting the respective front edge 107 and rear edge 108 of the panty liner 101, and a front section 109 and a rear section 110. The front section 109 and the rear section 110 do not necessarily divide the panty liner 101 into two equal-length parts. As can be seen from FIG. 1, the panty liner is shaped with a substantially rounded front section 109, which tapers towards the rear section 110. The side edges 105, 106 of the panty liner 101 are in this case somewhat curved.

The panty liner 101 further has a centre line 111 extending in the longitudinal direction. This means a line extending in the panty liner 101, which line is arranged equidistant from the longitudinal side edges 105, 106 of the panty liner. The side edges 105, 106, the principal extent of which is in the longitudinal direction of the panty liner 101, have a bow shape arranged such that the side edges 105, 106 curve in towards the longitudinal centre line 111 of the panty liner so as to correspond to the leg band curvature on a thong. In the rear section 110, the side edges 105, 106 converge in the rounded rear edge 108. In the front section 107, the side edges 105,106 converge in the undulating front edge 107. It is also, of course, possible for any or all of the edges 105, 106, 107, 108 to have a straight shape.

The panty liner 101 further has a fastening member 112 arranged on the liquid-permeable surface layer 102, which is intended to be facing the user during use. The fastening member 112 is here arranged in the rear section 110 of the panty liner 101 along the longitudinal centre line 111.

The fastening member 112 has a fastening surface 113, which is the surface of the panty liner which is fastened to the body of the user during use, more precisely to the perineum of the user.

The fastening surface 113 is constituted by adhesive, for example low-adhesion, self-adhering adhesive, hydrogel or some other suitable material which has suitable fastening properties to skin and can be removed without causing discomfort. The self-bonding adhesive can be a foamed adhesive and can hence have a slight padding which provides extra softness in the fastening member 112, thereby imparting a comfortable feeling to the user.

The fastening surface 113 shown in FIG. 1 is circular in shape. Of course, other forms of fastening surface are also possible, such as, for example, rectangular, triangular, dot-shaped or dash-shaped, in which latter case dots and dashes may form regular or irregular patterns.

As can be seen from FIG. 2, the liquid-permeable surface layer 102 has essentially the same shape as the absorption body 104. The liquid-blocking surface layer 103 is also shaped like the absorption body 104. The liquid-permeable surface layer 102, the liquid-blocking surface layer 103 and the absorption body 104 are joined together in a conventional manner, for example joined by gluing or by ultrasonic welding in a joint along the edges 105, 106, 107, 108 of the panty liner.

FIG. 2 shows a section through the panty liner 101 along the line II—II. The liquid-permeable surface layer 102 is conventional in type and can thus consist of any kind of liquid-permeable material which is suitable for the purpose. Examples of such materials are various types of thin non-woven materials, perforated plastics films, gauze material, liquid-permeable foam material, or the like. The liquid-permeable surface layer 102 can be made up of two or more different materials in order to provide various functions in the surface layer. It is customary, for example, to arrange a liquid-transporting layer in front of a liquid-admitting layer. It is further known to arrange different types of material on different parts of the surface of the panty liner 101 which is facing the user during use. Thus a material offering good admissibility can advantageously be arranged in the wet region, whilst sections of the surface layer which shall primarily constitute a bearing surface against the body of the user are provided with a material which has been enhanced in terms of softness and kindness to the skin.

As described in PCT/SE97/00167, the liquid-permeable surface layer 102 can also consist of a first layer of conventional, hydrophobic, liquid-permeable material. Such materials are usually treated by chemical or physical means to create a hydrophilic, wettable surface on the material. The first layer is fitted over the surface of the absorption body 104 which is intended to be facing the user during use. Examples of suitable surface materials are perforated plastics films, non-wovens made from hydrophobic fibres, plastics gauzes, or the like. Such a surface material lets fluid through to the absorption body 104 within. Since the absorption body 104 is more hydrophilic than the material in the surface layer, the surface material is almost fully drained of fluid. For this reason and since the surface material has essentially no absorbency, the surface material remains dry even after wetting. Only a very small quantity of fluid can remain on or in a hydrophobic surface layer of this kind When the sanitary towel 101 is used, this is placed in the region of the genitalia of the user, with a section situated next to the vaginal opening of the user. Secreted body fluid will consequently meet the sanitary towel 101 within a limited surface area of the sanitary towel 101, the wet region as it is known. Within the wet region, the liquid-permeable surface layer 102 can therefore have a second, hydrophilic and absorbent layer or can be treated so that the material within the wet region is more hydrophilic than surrounding sections of the liquid-permeable surface layer 102. Examples of suitable hydrophilic materials are non-woven materials comprising rayon, cotton, cellulose fibres, or the like.

It is not necessary to the invention for the liquid-permeable surface layer 102 to be constituted by a separate material layer; but rather the surface layer 102 can be a surface on the absorption body 104 of the panty liner 101. In such an embodiment, it is however especially expedient to provide the panty liner 101 with some form of liquid barriers which prevent fluid from being transported in the absorption material right out to the edges of the panty liner 101. Examples of such liquid barriers are compressions, welds, glue strands, doubled-over plastics strips, or hydrophobieizing agents such as wax, or the like.

The liquid-blocking surface layer 103 can be formed from any kind of liquid-tight material which is suitable for the purpose. Commonly occurring barriers layers are thin plastics films, for example made from polyethylene or polypropylene. It is also, however, possible to use impermeable non-woven materials, impermeable foamed materials, or the like. Coating with liquid-tight material also occurs. The liquid-tight surface layer can be air-permeable and steam-permeable, but impervious to fluid. It can further be advantageous to use stretchable, or elastically stretchable barrier layers.

The absorption body 104 can be an airlaid cellulose body, as it is known.

Other suitable absorbent materials for use in the absorption body 104 are, for example, cellulose fluff material, absorbent bonded fibre layers, tissue layers, absorbent foam, peat, or the like. The absorption body 104 can further contain superabsorbent polymers, i.e. polymers with the capacity to absorb many times their own weight of liquid in forming a liquid-containing gel. Superabsorbents usually exist in the form of particles, flakes, fibres, granules or the like. The superabsorbent material can appear singly or together with another absorbent material.

Figure 3:
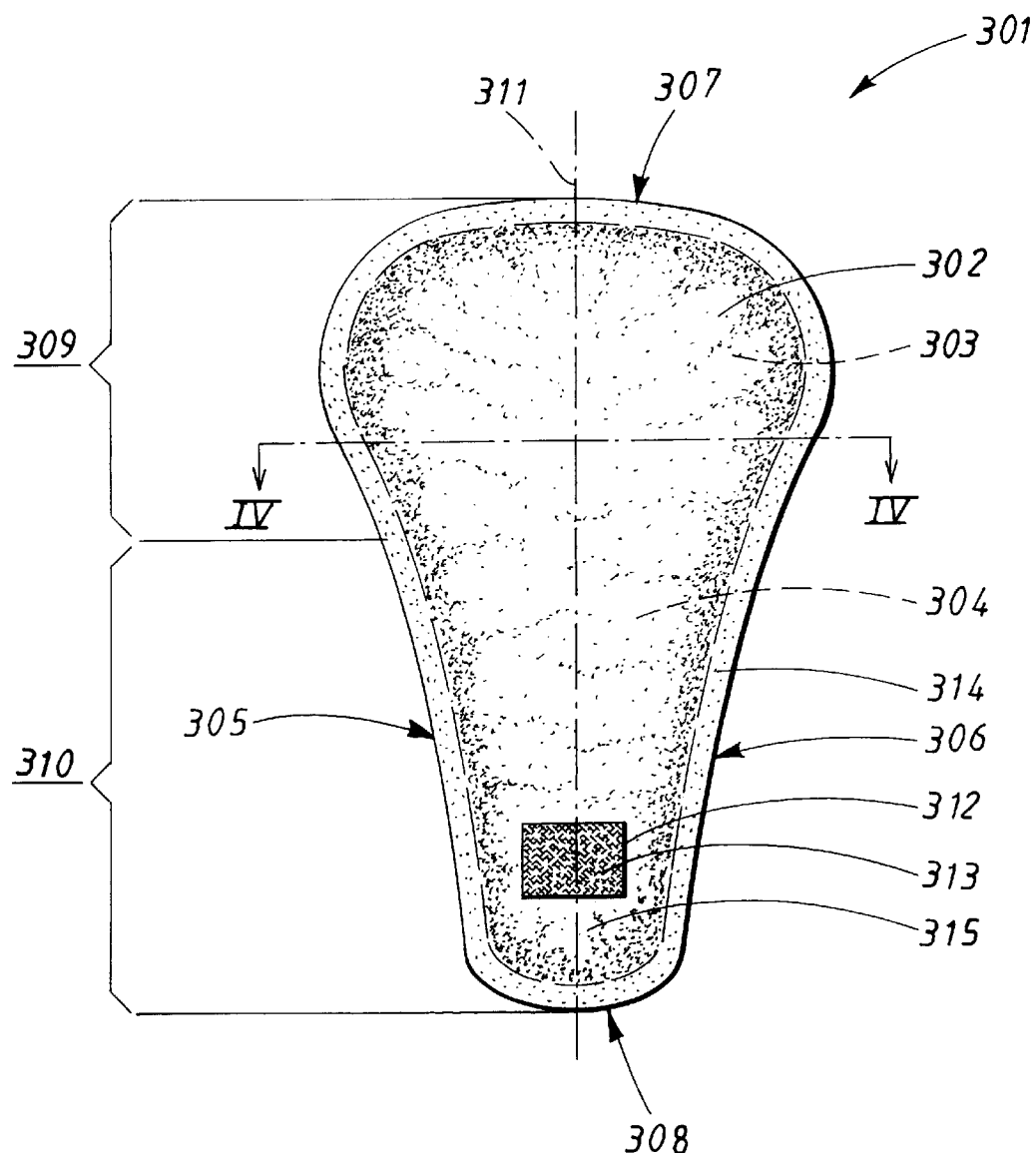
FIG. 3 shows a plane view of a sanitary towel viewed from the side which is intended to be facing the user when the sanitary towel is in use.
Figure 4:
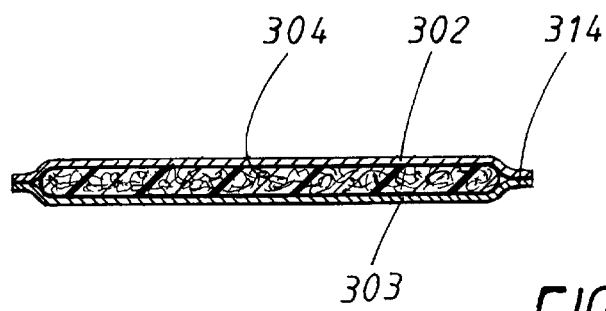
FIG. 4 shows a section along the line IV—IV through the sanitary towel in FIG. 3.

FIGS. 3 and 4 show a sanitary towel 301 having an essentially triangular shape with a longitudinal direction and a transverse direction. The sanitary towel 301 comprises a liquid-permeable surface layer 302, a liquid-blocking surface layer 303 and an absorption body 304 arranged between these surface layers 302, 303. The liquid-permeable surface layer 302 has essentially the same shape as the absorption body 304, but with a somewhat larger extent in the plane, whereby it forms a protruding edge around the whole of the periphery of the absorption body. The liquid-blocking surface layer 303 is also shaped like the absorption body 304, but with a somewhat larger planar extent than the latter. The surface layers 302, 303 are joined together outside the absorption body 304, for example by gluing, sewing or thermal or ultrasonic welding, forming a protruding casing edge 314.

The sanitary towel 301 has two longitudinal side edges 305, 306, a front edge 307 and a rear edge 308. The sanitary towel 301 further has a front section 309 and a rear section 310. The front section 309 and the rear section 310 do not necessarily divide the sanitary towel into two equal-length parts.

The sanitary towel 301 also has a centre line 311 extending in the longitudinal direction. This means a line extending in the sanitary towel 301, which line is arranged equidistant from the longitudinal side edges 304, 305 of the panty liner. The side edges 305, 306, the principal extent of which is in the longitudinal direction of the sanitary towel 301, have a bow shape arranged such that the side edges 305, 306 curve in towards the longitudinal centre line 311 of the panty liner so as to correspond to the leg band curvature on a thong. In the rear section 310, the side edges 305, 306 converge in the rounded rear edge 308. In the front section 307, the side edges 305, 306 converge in the rounded front edge 307.

The liquid-permeable surface layer 302, the liquid-blocking surface layer 303 and the absorption body 304 can be constituted, for example, by the materials specified for the liquid-permeable surface layer 102, the liquid-blocking surface layer 103 and the absorption body 104 in connection with FIGS. 1 and 2.

In order to obtain increased absorption capacity in the sanitary towel, this can be provided with a longitudinal elevation (not shown in the figure). Advantageously, such an elevation is placed in the wet region, i.e. the section of the sanitary towel which is first expected to be wetted by the majority of the body fluid. A sanitary towel intended for wear in connection with a thong has a very narrow rear section, which means that the available liquid-receiving surface is small. It can therefore be expedient for the elevation to comprise superabsorbent materials capable of absorbing large quantities of body fluid in relation to their volume. It is also, of course, possible for the elevation to be of similar construction to the absorption body 304.

The panty liner 301 further has a fastening member 312 intended to be fastened to the perineum of the user. The fastening member 312 is arranged on the liquid-permeable surface layer 302, which is intended to be facing the user during use. The fastening member 312 is here arranged in the rear section 310 of the panty liner 301 along the longitudinal centre line 311. In the embodiment shown in FIG. 3, the fastening member 312 is arranged at a distance from the rear edge 308 such that a tongue 315 is formed between the periphery of the fastening member 312 and the rear edge 308 of the product 301. The distance from the rear edge 308 of the product to the periphery of the fastening member 312 should be max. 10 mm. The reason why it is preferred to limit the length of the tongue 315 is that there is otherwise the risk that a long tongue 315 might be displaced during use and hence cause discomfort to the user. Moreover, some of the discretion which is sought with a thong would thereby be forfeited.

The fastening surface 313 of the fastening member 312 can be constituted by a similar adhesive to that specified for the fastening surface 113 in connection with FIG. 1.

The fastening surface 313 in FIG. 3 has a rectangular shape, but it can, of course, have similar shapes to those specified for the fastening surface 113 in connection with FIG. 1.

It is, of course, possible, within the scope of the invention, to arrange the fastening surface in any kind of pattern or shape which is suitable for the purpose. It is also obviously possible to arrange the fastening surface such that it extends out to the side edges of the product and/or out to the rear edge of the product.

Although the invention has been described in connection with a panty liner and a sanitary towel, the invention can obviously be applied to other types of absorbent products intended to be used by women and worn inside a thong.

Before the absorbent product is used, the fastening surface is protected in a conventional manner, for example by covering with a protective layer of paper or plastic which has been silicone-treated or stamped to allow easy detachment as the product is about to be used. The fastening surface can, of course, be covered with any other suitable protection which is easily detachable.

It is also, of course, possible, within the scope of the invention, to combine the shown embodiments one with another.

What is claimed is:

1. An absorbent article having a longitudinal direction and a transverse direction, comprising a liquid-permeable surface layer, a liquid-blocking surface layer and an absorption body arranged between the two surface layers, two side edges extending substantially in the longitudinal direction, a front edge, a rear edge, a front section and a rear section the rear section having a width not exceeding 40 mm, and a fastening member intended to be fastened to the body of a user, wherein the product is essentially triangular in shape and the fastening member is applied to the liquid-permeable surface layer only in the rear section of the absorbent article.

2. The absorbent article according to claim 1, in which the fastening member has a fastening surface which is constituted by a low-adhesion, self-adhering adhesive.

3. The absorbent article according to claim 1, in which the fastening member has a fastening surface which is constituted by a hydrogel.

4. An absorbent product according to claim 3, in which the hydrogel comprises polymers based on vinyl alcohol, polyacrylate, polymethacrylate, polyethylene oxide, polysaccharide, acrylamide, vinyl pyrrolidone, polyethers, amino acids or urethane, and mixtures, copolymers and derivatives thereof.

5. The absorbent article according to claim 1, in which the side edges of the product are curved in a direction in towards a centre line extending in the longitudinal direction of the product.

6. The absorbent article according to claim 1, in which the fastening surface has a maximum width of 15 mm and a maximum length of 20 mm.

7. The absorbent article according to claim 1, in which the distance from the rear edge to a periphery of the fastening member is a maximum of 10 mm.

8. The absorbent article according to claim 1, in which the rear section of the product, in the region of the fastening member, has a maximum width of 20 mm.

9. The absorbent article according to claim 1, in which the length of the product is no greater than 260 mm.

10. The absorbent article according to claim 1, in which at least one component of the product has an intrinsic rigidity of at least 100 N, measured according to ASTM D 4032-82 "Circular Bend Procedure".

11. The absorbent article according to claim 1, in which the product is a sanitary towel, a panty liner, or an incontinence pad.

* * * * *